March 2, 1954 TAIJIRO KASUGA Plant Pat. 1,264
STRAWBERRY PLANT
Filed April 23, 1953
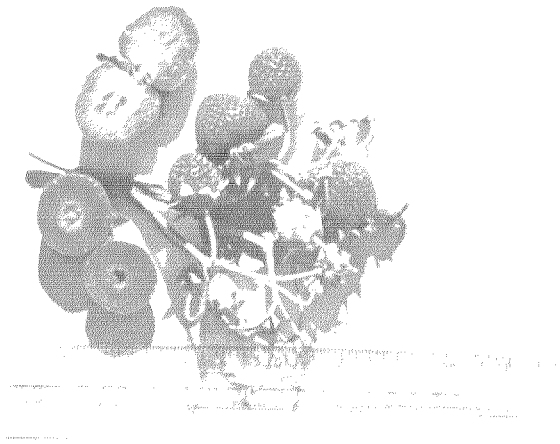
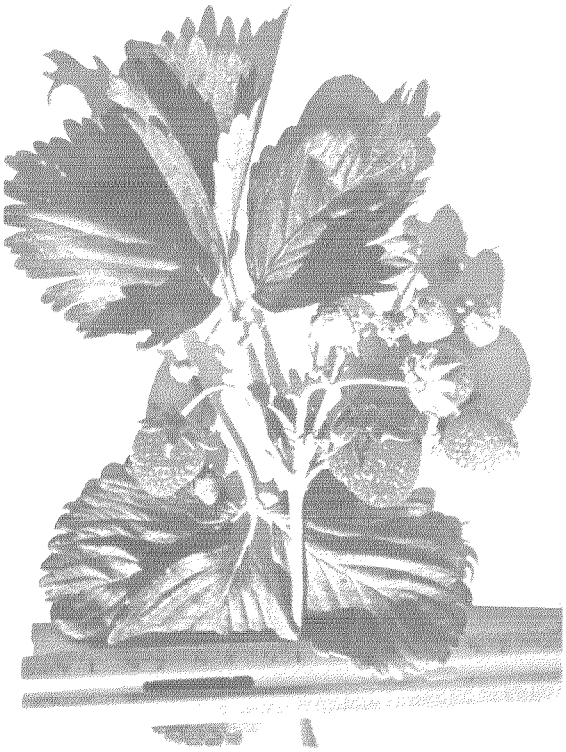
Inventor.
Taijiro Kasuga
By: Robert Robb
Attorneys Patented Mar. 2, 1954

Plant Pat. 1,264

UNITED STATES PATENT OFFICE 1,264

STRAWBERRY PLANT

Taijiro Kasuga, Sandy, Utah

Application April 23, 1953, Serial No. 350,786

1 Claim. (Cl. 47—62)

The present invention relates to a new and distinct variety of strawberry plant which was originated by me by crossing the variety "Starbright" (unpatented) with the variety "Twentieth Century" (unpatented).

My new variety of strawberry plant is endowed with an unusual combination of characteristics which distinguish it from its parents, as well as from all other varieties of its class. The following are perhaps the most outstanding of these improved characteristics:

(1) A relatively long bearing season, starting at about the same time as the parent "Starbright";

(2) Every new plant bears fruit, and this is a very important advantage which differentiates my new variety from many others, including "Starbright";

(3) The fruit is very uniform in shape, somewhat darker in color than that of the variety "Starbright," and averages somewhat larger in size than the fruit of either parent, with the size holding up well until the end of the bearing season;

(4) The fruit is free from "nubbins" or "buttons" which are characteristic of many other strawberry varieties, and has excellent holding and shipping qualities, with retention of firmness even under moist conditions;

(5) The plants of my new variety stand up much better than most other varieties under high salt or alkali soil conditions; and (6) The fruit of my new variety has excellent qualities for desserts, makes good jam, and is suitable for many other table uses, as well as for canning purposes.

In comparison with its parents, my new variety more favorably compares with its parent "Twentieth Century," yet is distinguished from both parents to a marked extent. The plants of my new variety are taller, less-branched, but more vigorous than those of "Twentieth Century," and are more resistant to mildew and to thrip damage than those of this parent, while they are equally resistant to frost, and are superior to "Twentieth Century" in drought and alkali resistance. The leaves of my new variety are fewer in number but larger than those of the parent "Twentieth Century"; the blade of the central leaflet on my new variety equals those of the laterals, while in the case of "Twentieth Century," the blade of the central leaflet is two or three times as long as those of the laterals. The leaf serrations of both varieties are quite similar, but the leaf surface of "Twentieth Century" is not as wrinkled as that of my new variety, and has less tendency to curl upward. In respect to color, the leaves of my new variety are somewhat lighter on both the upper and lower surfaces, and the pubescence on the leaves of my new variety is somewhat less abundant than in "Twentieth Century."

The runners of my new variety appear during the fruiting season, as in the variety "Twentieth Century," but are more numerous, stouter and nearly twice as long as those of this parent.

The flower stems of my new variety are longer than those of "Twentieth Century," yet the inflorescence of both varieties is protected by their foliage. The date of bloom and the number of flowers of my new variety are approximately the same as "Twentieth Century," but the flowers of my new variety are almost twice the size of those of "Twentieth Century." Both varieties have perfect flowers, their pollen is medium in abundance, and the filaments of the stamen are similar in length. The fruiting stems of my new variety are generally similar to those of "Twentieth Century," being short, stout and upright. The radical is much shorter in my new variety than in "Twentieth Century," but the branches of the truss are approximately the same in number.

The fruiting season of my new variety runs from about June 1st to July 15th, whereas "Twentieth Century" usually bears only one heavy crop during this same period, and another heavy crop in the autumn, with some additional fruit produced throughout the summer. However, the fruit of my new variety is very uniform in shape, as contrasted with the exceedingly variable shape of the fruit of "Twentieth Century." Both varieties have relatively large fruit, but that of "Twentieth Century" has a tendency to decrease in size later in the fall, whereas the fruit of my new variety holds up well in size throughout the season. Many berries of the "Twentieth Century" variety are wedge-shaped, whereas those of my new variety are uniformly round-conic. The color of the fruit of my new variety usually runs from Scarlet Red to Carmine, whereas the color of the fruit of "Twentieth Century" is Scarlet Red or lighter shades thereof. The stems of the fruit and the main trusses of my new variety are stout and short, whereas those of "Twentieth Century" are more slender, while the pubescence on the stems of the fruit is abundant and ascending in each variety. The calyx of my new variety is much larger than that of "Twentieth Century," remains green after picking, is even with the fruit surface, and otherwise resembles that of "Twentieth Century." Pubescence on the calyx is abundant in my new variety, and the color is Light Green as in "Twentieth Century," with the segments ranging from 12 to 14 in my new variety, as compared with 10 to 14 in the case of "Twentieth Century." The form of the calyx in my new variety is acuminate, whereas that of "Twentieth Century" is oval and acute. The surface of the berry is glossy in both varieties, while the seeds of my new variety are less conspicuous and are depressed slightly below the surface, as distinguished from the conspicuous and projecting seeds of "Twentieth Century." All seeds are fertile in both varieties, while those of my new variety are somewhat smaller than those of "Twentieth Century," with no markings showing on the seeds of either variety.

The fruit of my new variety is more firm and finer texture than the relatively soft, coarse fruit of "Twentieth Century." Although the flavor of the fruit of my new variety is not quite as sweet as that of "Twentieth Century," the fruit of my new variety has much more aroma.

Asexual reproduction of my new variety by layering at Sandy, Utah, shows that the foregoing characteristics and distinctions come true to form and are established and transmitted through succeeding propagations.

The accompanying drawing shows specimens of the fruit, stems and foliage of my new variety in different stages of development, with certain of the fruit specimens shown in longitudinal as well as in transverse cross-section.

The following is a detailed description of my new variety as based upon specimens grown and observed at Sandy, Utah, with color terminology in accordance with Ridgway's Color Standards and Nomenclature (1912 Edition):

Dates of first and list picking: From about June 1st to about July 15th.

Plant:

*Growth.*—Vigorous.

*Root.*—Vigorous.

*Crown.*—Mostly simple, with some branches; medium size.

Leaves: Few; medium size.

*Petiole.*—Medium length; slender; petiole of central leaflet is ½ longer than that of lateral leaflets; central leaflet blade equals lateral. Color—Lettuce Green, Plate V; half with bracts and half without bracts.

*Pubescence.*—Scant; appressed.

*Groove.*—Shallow.

*Serrations.*—Regular; broadly ovate; ciliate; apex colored Green; serrations of central leaflet extend over upper ⅔ of margin but over ¾ of margin of lateral leaflets.

*Leaflet surface.*—Upper side—glossy; rugose; almost glabrous; wrinkled; curled upward. Color—Antique Green, Plate VI. Lower side—color—Light Bice Green, Plate XVII. Pubescence—scant.

Runners: Appear during fruiting; numerous; medium length; 40 to 48 cm. long.

Flower stems: Medium length; about 80 mm. long; inflorescence protected by foliage.

Bloom: Medium size.

*Date first bloom.*—About May 1st.

*Date full bloom.*—About May 15th.

*Flowers.*—Many; perfect. Breadth (primary)—50 mm. Breadth (secondary)—35 to 45 mm. Color—white.

*Filaments of stamens.*—Mostly long, but some short.

*Pollen.*—Medium abundance.

Fruiting stems: Short; stout; upright; radical equals main truss; few truss branches.

Soil where grown: Sandy; well-drained.

Culture: Shallow; 3 or 4 cultivations required, but no mulching; preferably sprayed with D. D. T. and Parathion for leaf roller just before bloom.

Resistance: (as compared with other varieties grown under comparable cultural conditions at Sandy, Utah):

*Disease.*—Plant—good resistance to mildew; fruit—no diseases observed to date.

*Insect.*—Good resistance to thrips.

*Frost.*—Good.

*Drought.*—Medium.

*Alkali.*—Good.

Fruit:

*Condition when described.*—Prime.

*Date described.*—June 8th.

*Size.*—Uniform; large; constant throughout season. Length—average 30 mm.; breadth—average 30 mm.; thickness—average 30 mm.

*Form.*—Uniform; regular; round-conic; apex rounded.

*Stems*—Radical—stout; short. Main truss—stout; short. Pubescence—abundant; ascending.

*Calyx.*—Green after picking; even with fruit surface; free; large. Upper surface: Color—Hayes Green, Plate XVIII; pubescence—abundant. Lower surface: Color—Rainette Green, Plate XXXI; pubescence—abundant. Segments—12 to 14 in number. Length—15 mm.; breadth—5 mm. Form—acuminate.

*Surface.*—Glossy. Color—Spectrum Red, Plate I, with few green tips. Seeds—inconspicuous; depressed slightly below surface; lower seeds fertile; medium number. Size—small. Color—Buff Yellow, Plate IV, with no markings.

*Core.*—Hollow. Color—Hermosa Pink, Plate I.

*Flesh.*—Juicy. Color—Rose Red, Plate XII. Texture—firm; fine; crisp.

*Flavor.*—Sweet; aromatic.

*Quality.*—Best. Shipping quality—excellent.

*Use.*—Market; local; canning; dessert.

I claim:

A new and distinct variety of strawberry plant, substantially as herein shown and described, characterized particularly as to novelty by its relatively long bearing season, by the unusually reliable fruit-bearing habit of every new plant, by the relatively large size and very uniform shape of its fruit, by its habit of holding the large size of its fruit to the end of the fruiting season, by the freedom of its fruit from nubbins or buttons, by the excellent holding and shipping qualities of its fruit and the retention of firmness of the fruit under moist conditions, by the distinctive color and superior aroma of its fruit, and by its superior resistance to high salt and alkali soil conditions.

TAIJIRO KASUGA.

No references cited.